US009775659B2

(12) United States Patent
Cheney et al.

(10) Patent No.: US 9,775,659 B2
(45) Date of Patent: Oct. 3, 2017

(54) METHOD AND SYSTEM FOR STORING AND INSERTING AN IMPLANT

(71) Applicant: BioMedical Enterprises, Inc., San Antonio, TX (US)

(72) Inventors: Daniel F. Cheney, San Antonio, TX (US); Eric A. Marcano, San Antonio, TX (US); David J. Pancratz, Helotes, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 511 days.

(21) Appl. No.: 14/450,654

(22) Filed: Aug. 4, 2014

(65) Prior Publication Data

US 2014/0343615 A1 Nov. 20, 2014

Related U.S. Application Data

(62) Division of application No. 12/924,733, filed on Oct. 4, 2010, now Pat. No. 8,834,483.

(51) Int. Cl.
*A61B 17/68* (2006.01)
*A61B 17/84* (2006.01)
(Continued)

(52) U.S. Cl.
CPC ........ *A61B 17/844* (2013.01); *A61B 17/8872* (2013.01); *B65B 5/04* (2013.01); *A61B 17/68* (2013.01); *A61B 2017/00867* (2013.01)

(58) Field of Classification Search
CPC .... A61F 2/0095; A61F 2/4225; A61F 2/4241; A61F 2/4606;
(Continued)

(56) References Cited

U.S. PATENT DOCUMENTS 5,120,175 A 6/1992 Arbegast et al.
5,171,252 A 12/1992 Friedland
(Continued)

FOREIGN PATENT DOCUMENTS

CN 87101011 A 2/1988
EP 0326426 B1 12/1994
(Continued)

OTHER PUBLICATIONS

Prandi, Bernard, Development of a New Nitinol Implant for Hand Surgery, Proceedings of the International Conference of Shape Memory and Superelastic Technologies, Oct. 3-7, 2004, Kurhaus BadeBaden, Baden-Baden, Germany.
(Continued)

*Primary Examiner* — Kevin T Truong
*Assistant Examiner* — Tracy Kamikawa
(74) *Attorney, Agent, or Firm* — Christopher L. Makay

(57) ABSTRACT

An implant storage and insertion system for a shape memory orthopedic implant allows the implant to be constrained in a deformed state, protected, insulated, held for insertion, and properly positioned in bone. The implant storage and insertion system includes a restraining block having an impact surface. The restraining block engages an implant at a first end, and further a medical instrument engages the restraining block and positions the restraining block at a bone such that the impact surface may be impacted to insert a second end of the implant into the bone.

11 Claims, 17 Drawing Sheets

(51) Int. Cl.
*A61B 17/88* (2006.01)
*A61B 19/02* (2006.01)
*B65B 5/04* (2006.01)
*A61B 17/00* (2006.01)

(58) Field of Classification Search
CPC .. A61F 2002/4228–2002/4258; A61B 17/844;
A61B 17/846; A61B 17/865; A61B
17/88; A61B 17/885; A61B 17/8872;
A61B 17/8875; A61B 17/8894; A61B
17/064; A61B 17/0642; A61B 17/0644;
A61B 17/0682; A61B 2017/681; A61B
2017/0645; A61B 2017/0648; A61B
2017/0688; A61B 2017/0419; A61B
50/30; A61B 50/33; A61B 2050/005;
A61B 2050/0058; A61B 2050/006
See application file for complete search history.

(56) References Cited

U.S. PATENT DOCUMENTS

| | | | |
|---|---|---|---|
| 5,179,915 A | 1/1993 | Cohen et al. | |
| 5,281,225 A | 1/1994 | Vicenzi | |
| 5,358,405 A | 10/1994 | Imai | |
| 5,474,557 A | 12/1995 | Mai | |
| 5,882,351 A | 3/1999 | Fox | |
| 6,203,545 B1 | 3/2001 | Stofella | |
| 6,281,262 B1 | 8/2001 | Shikinami | |
| 6,290,719 B1 | 9/2001 | Garberoglio | |
| 6,332,885 B1 | 12/2001 | Martella | |
| 6,592,370 B2 | 7/2003 | Morgan | |
| 6,626,910 B1 | 9/2003 | Hugues | |
| 7,052,498 B2 | 5/2006 | Levy et al. | |
| 7,918,879 B2 | 4/2011 | Yeung et al. | |
| 8,162,942 B2 | 4/2012 | Coati et al. | |
| 8,262,712 B2 | 9/2012 | Coilard-Lavirotte et al. | |
| 8,394,097 B2 | 3/2013 | Peyrot et al. | |
| 8,475,456 B2 | 7/2013 | Augoyard et al. | |
| 2002/0165544 A1 | 11/2002 | Perren et al. | |
| 2004/0230193 A1 | 11/2004 | Cheung et al. | |
| 2005/0010228 A1 | 1/2005 | Medoff | |
| 2005/0043757 A1 | 2/2005 | Arad et al. | |
| 2005/0055027 A1 | 3/2005 | Yeung et al. | |
| 2005/0283159 A1 | 12/2005 | Amara | |
| 2008/0200984 A1* | 8/2008 | Jodaitis | A61F 2/442 623/17.16 |

FOREIGN PATENT DOCUMENTS

| | | |
|---|---|---|
| EP | 0821923 A1 | 2/1998 |
| EP | 0896813 A3 | 8/1999 |
| EP | 1079752 B1 | 1/2005 |
| EP | 1582164 A1 | 10/2005 |
| FR | 2787313 A1 | 12/1998 |
| JP | 1057398 A | 3/1998 |

OTHER PUBLICATIONS

A.W Anson, D.H.R. Jenkins, and S. Andrews, Development of a Nickel Titanium Shape Memory Alloy Bone Repair Staple and Other In-Vivo Orthopaedic and Cardio-Vascular Devices, Proceedings of tthe Technology Transfer Workshop, held at ESA/ESTEC, Noordwijk, The Netherlands, May 25-27, 1994 (ESA SP-364, Aug. 1994).

ARIM Soft Tissue Reattachment Anchor Brochure, MemoMetal, Inc., Oct. 26, 2008.

Smart Toe Orthopedic Implant Brochure, MemoMetal, Inc., Oct. 26, 2008.

X-Fuse Orthopedic Implant Brochure, MemoMetal, Inc., Oct. 26, 2008.

* cited by examiner

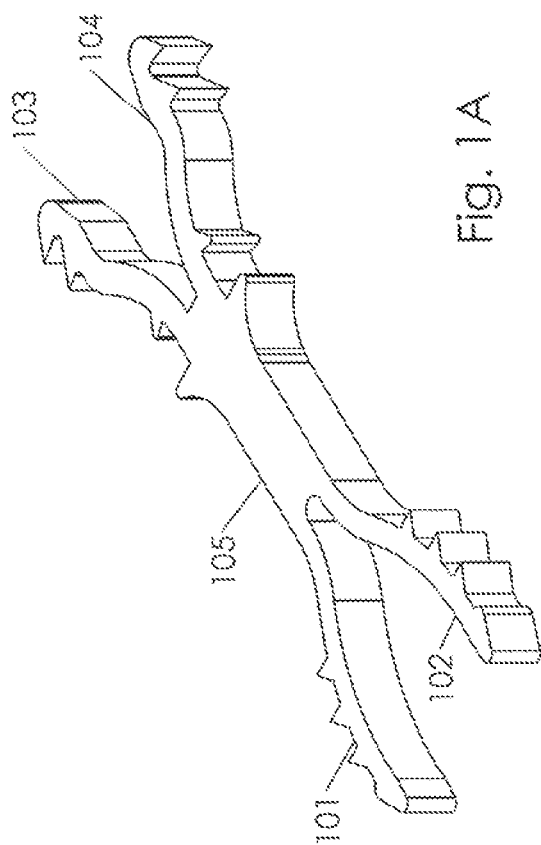
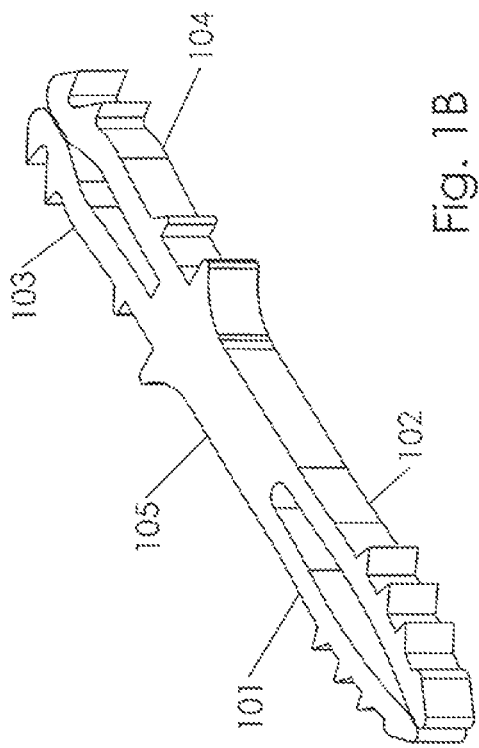
Fig. 1A
Fig. 1B

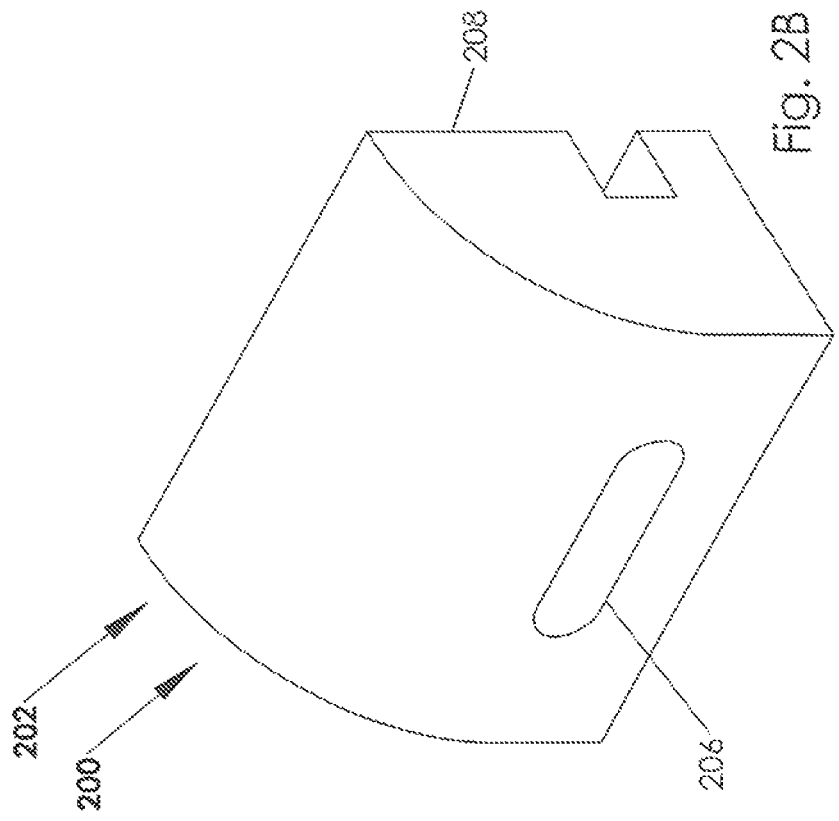
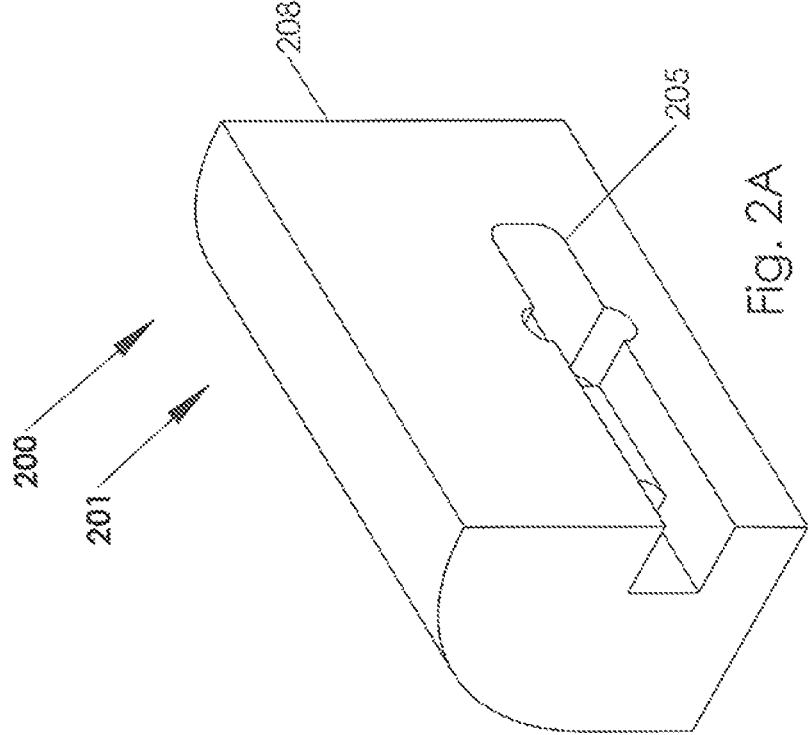

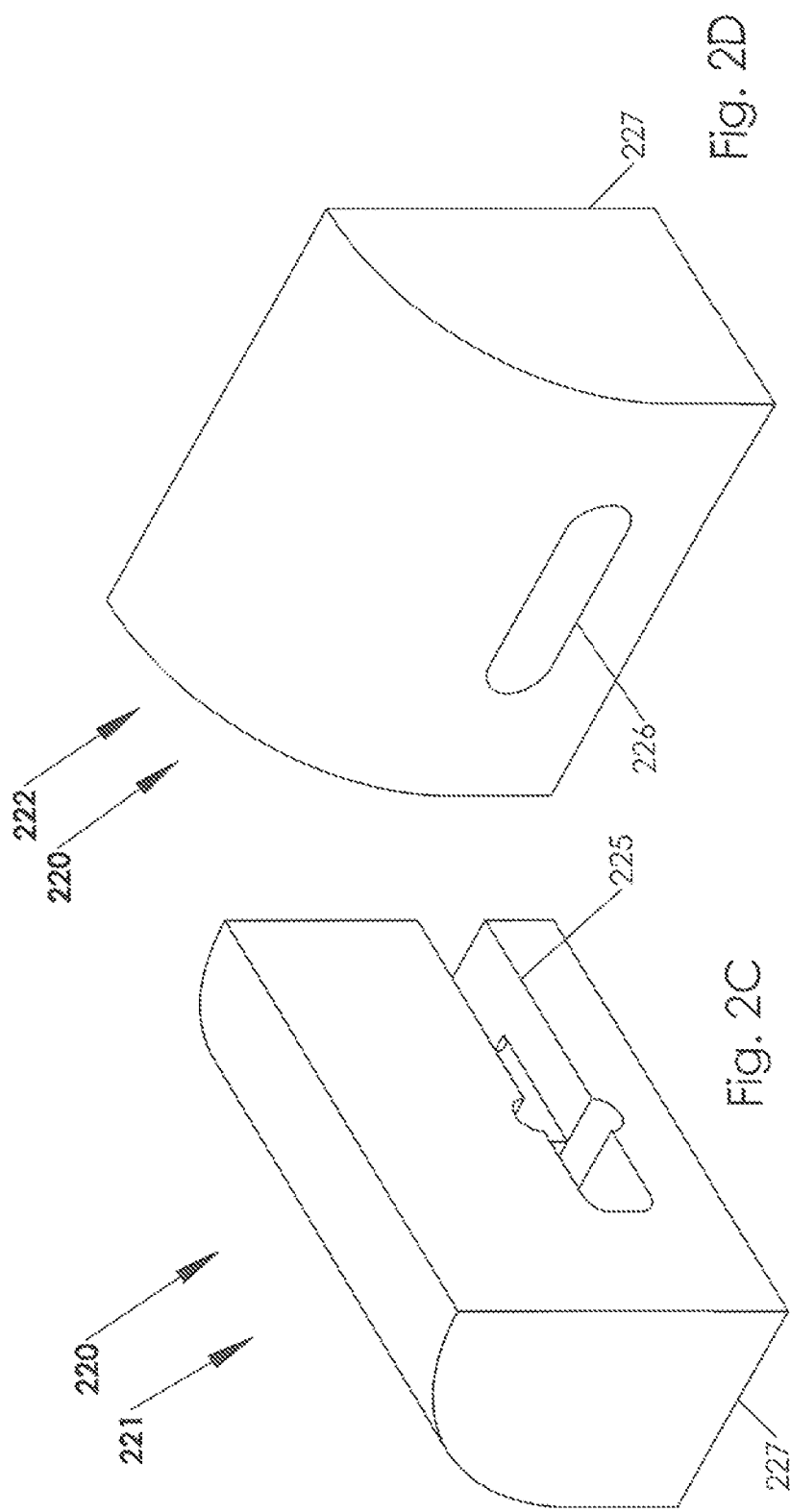

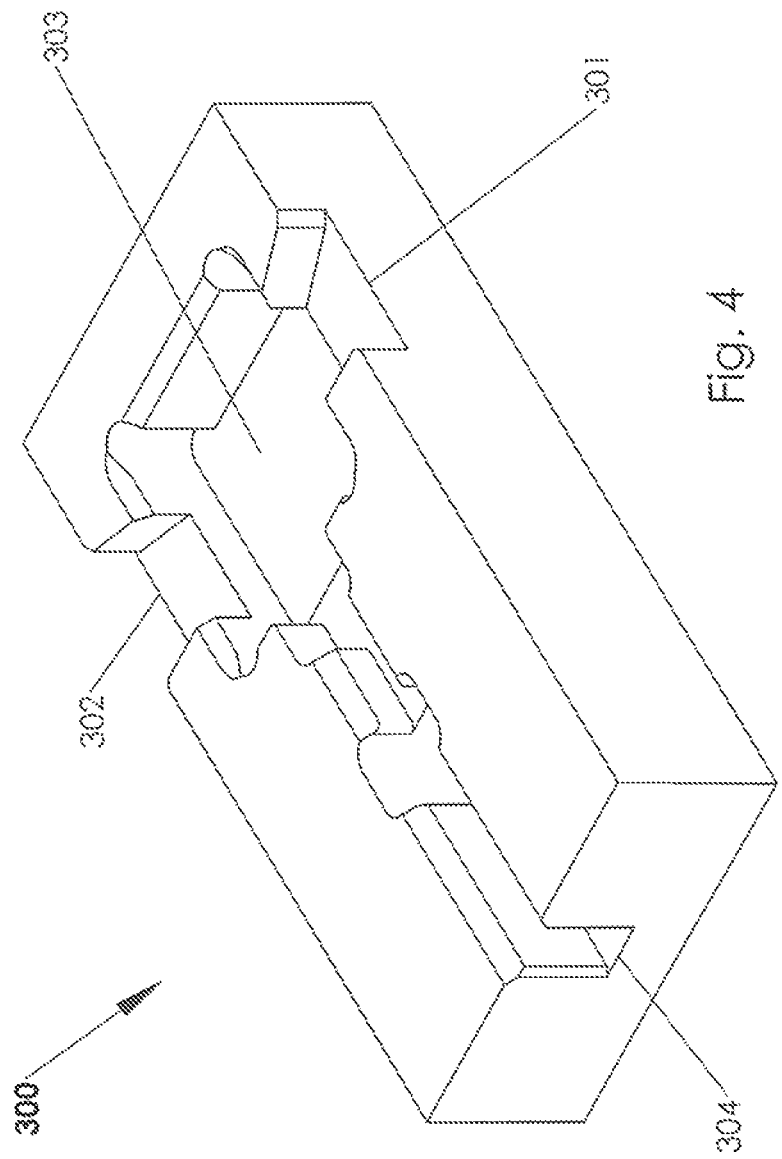

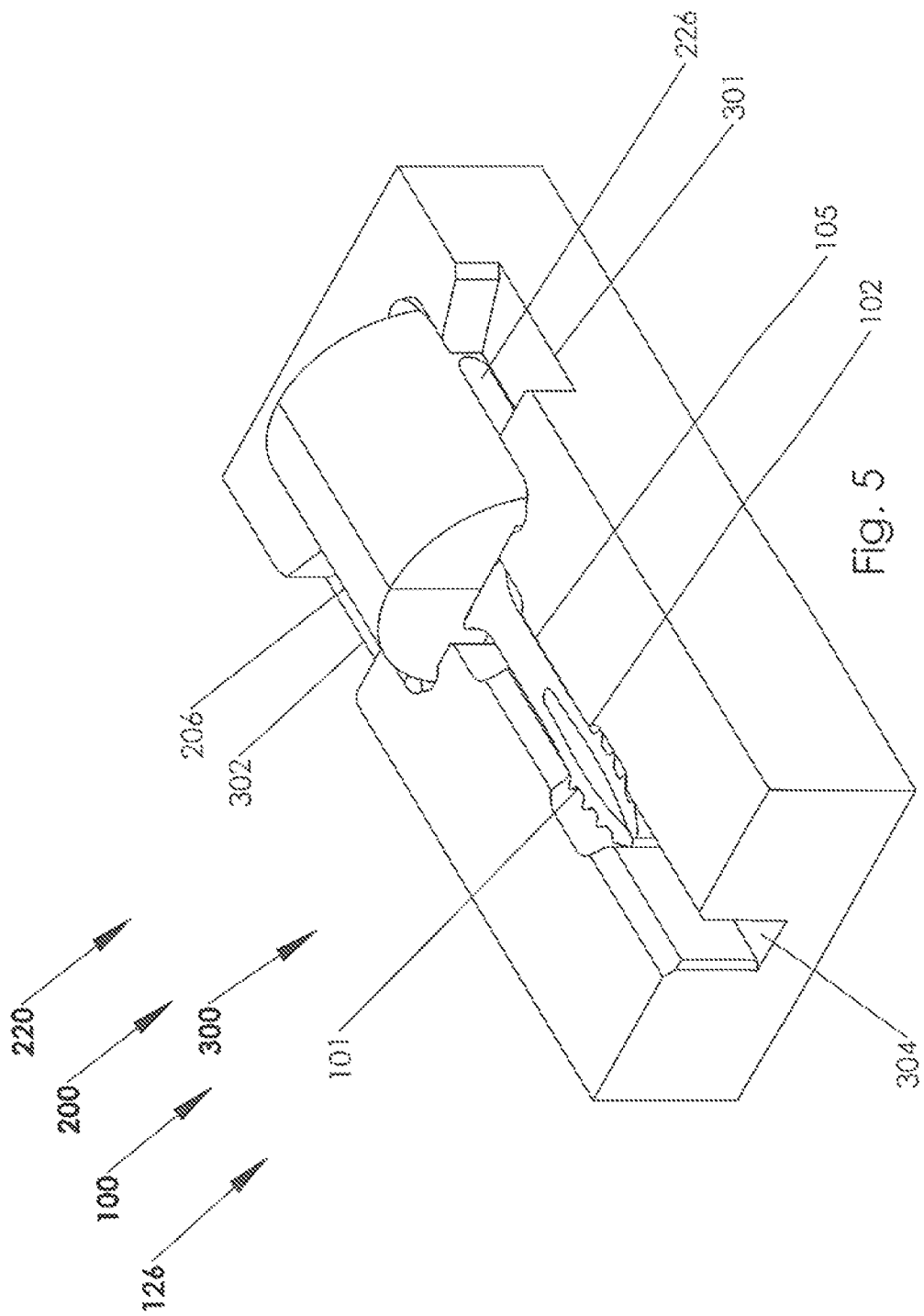

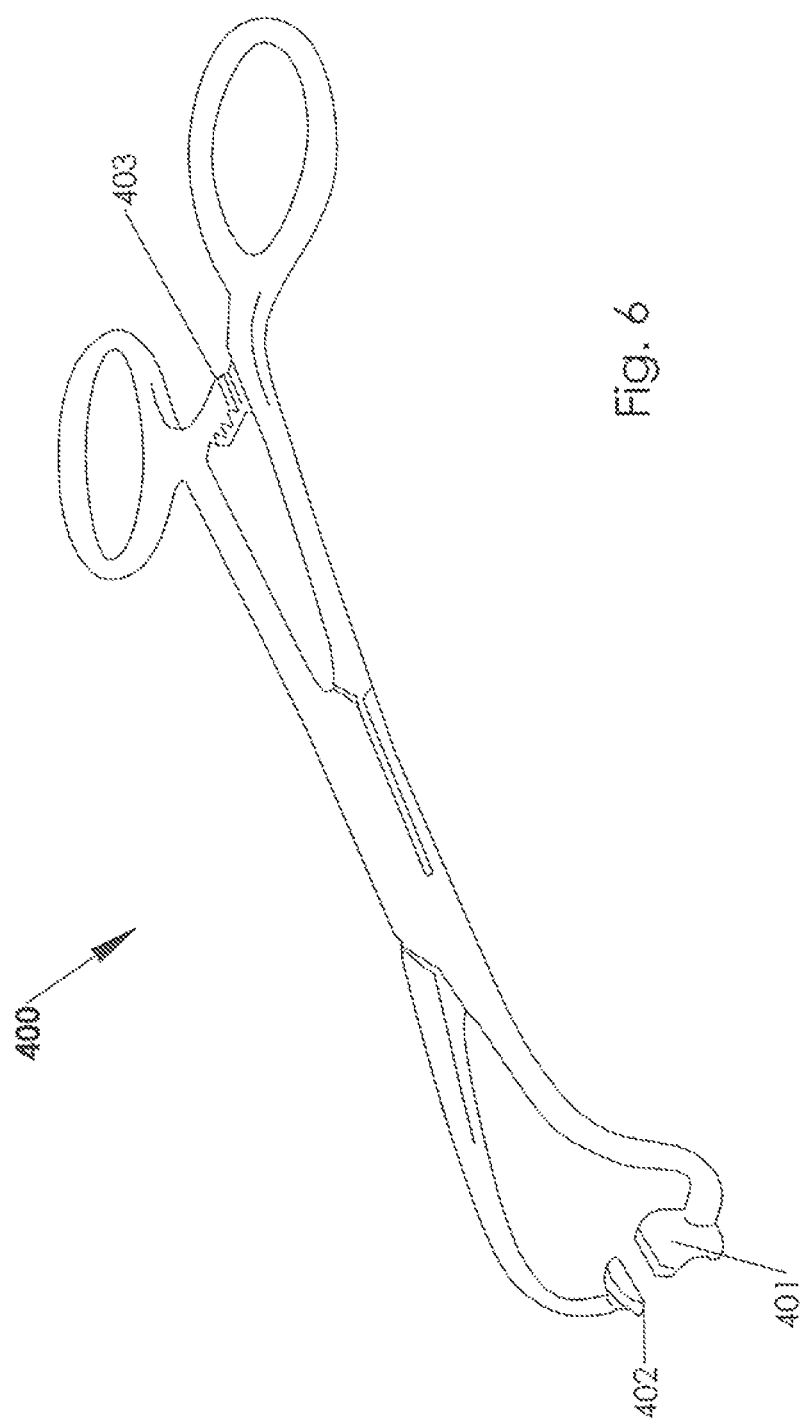

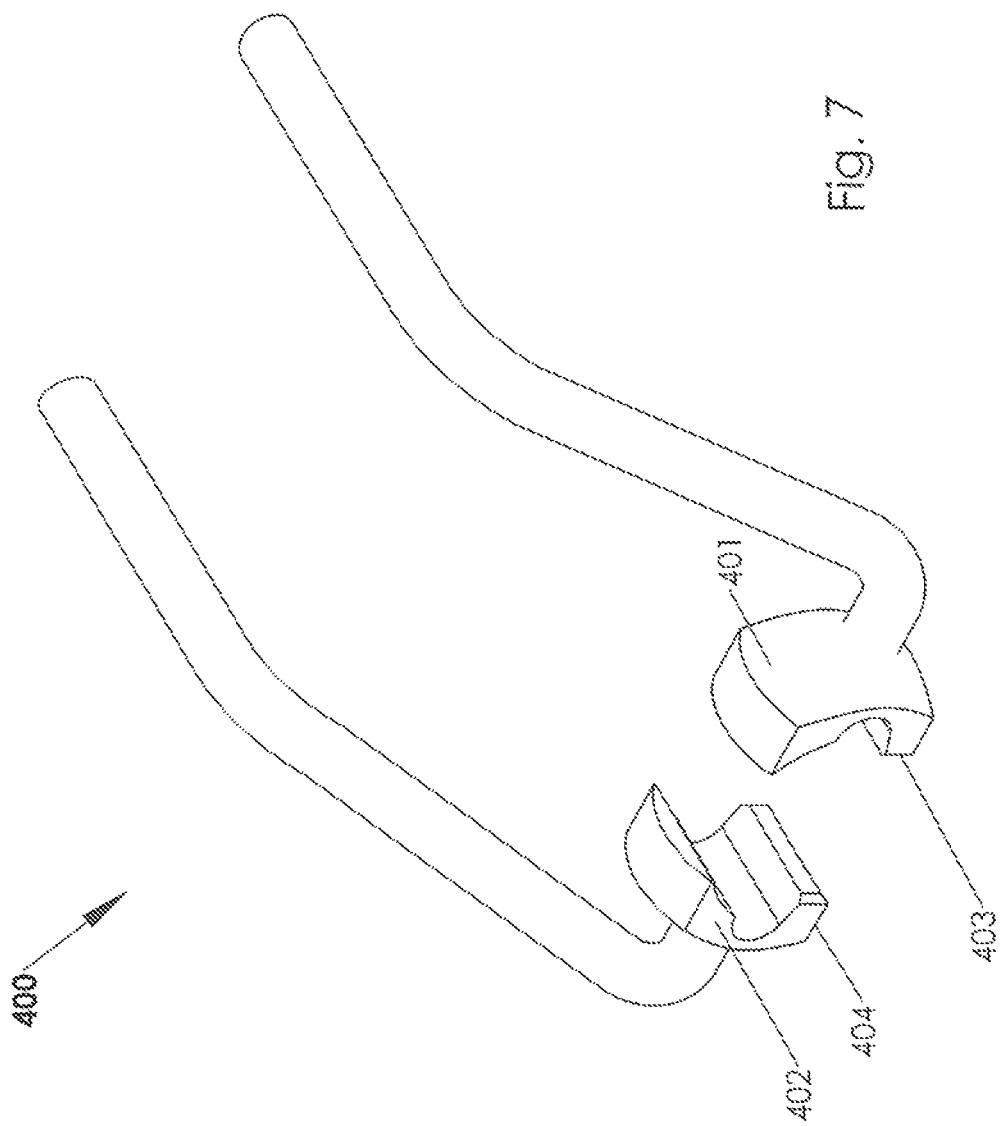

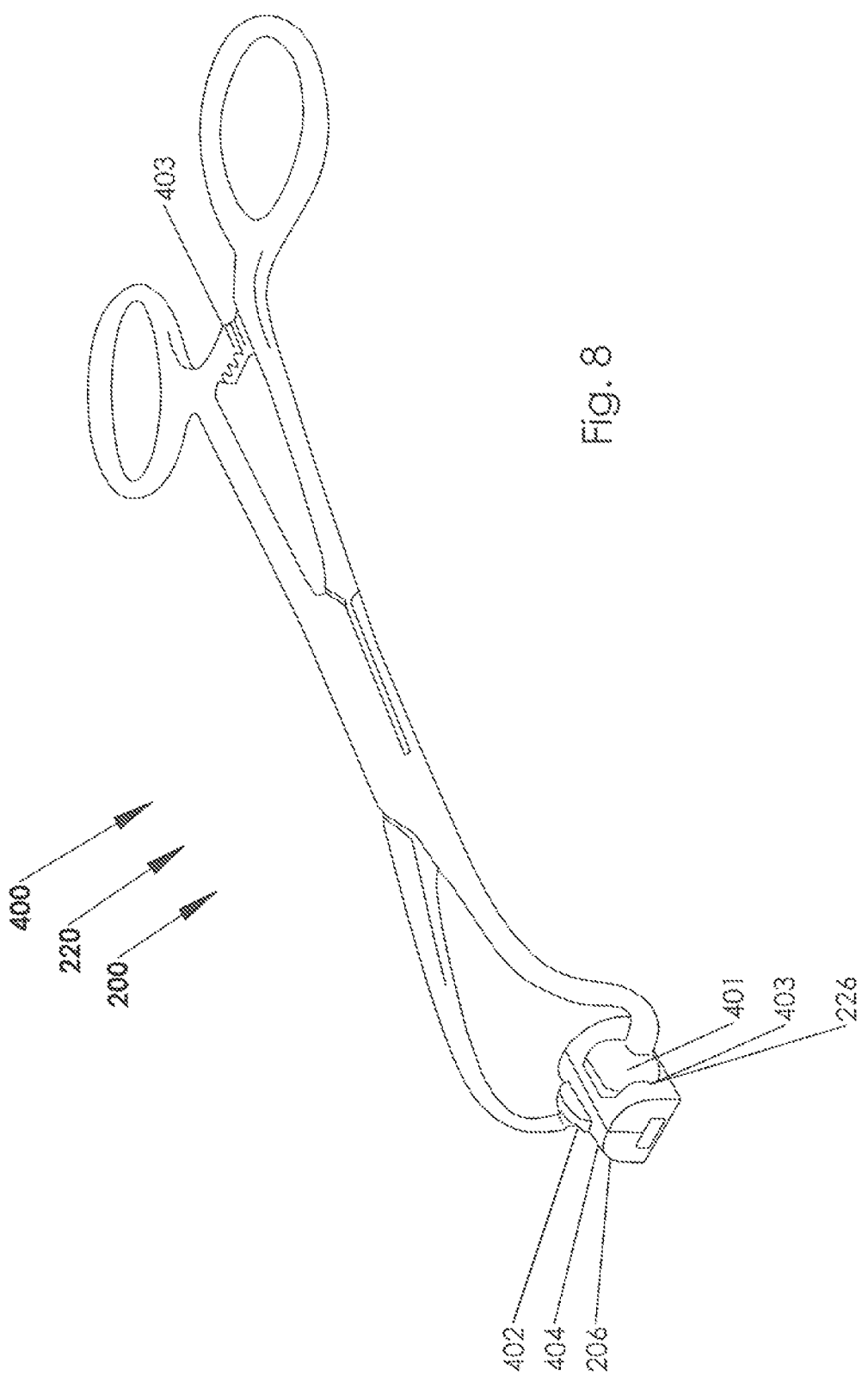

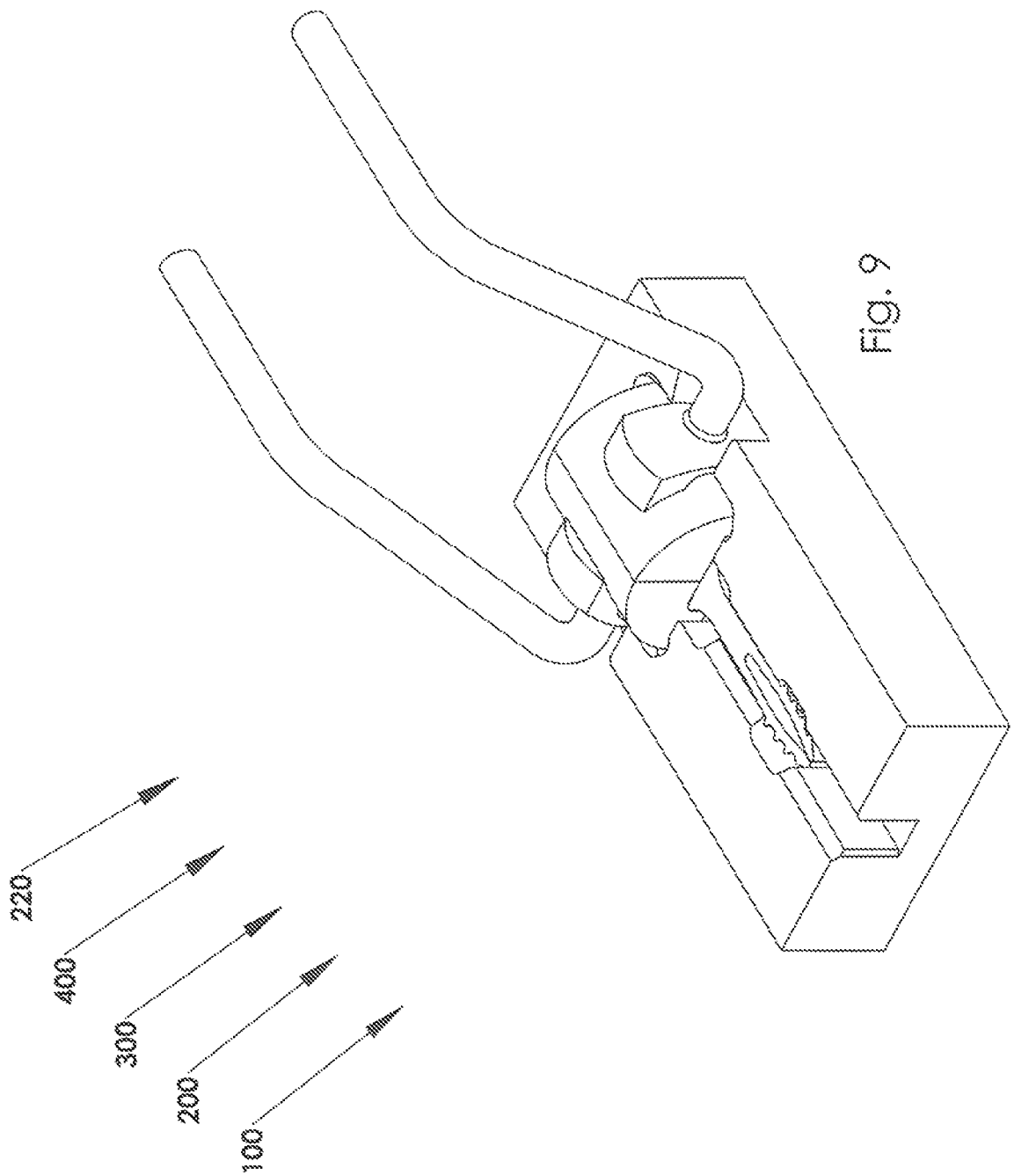

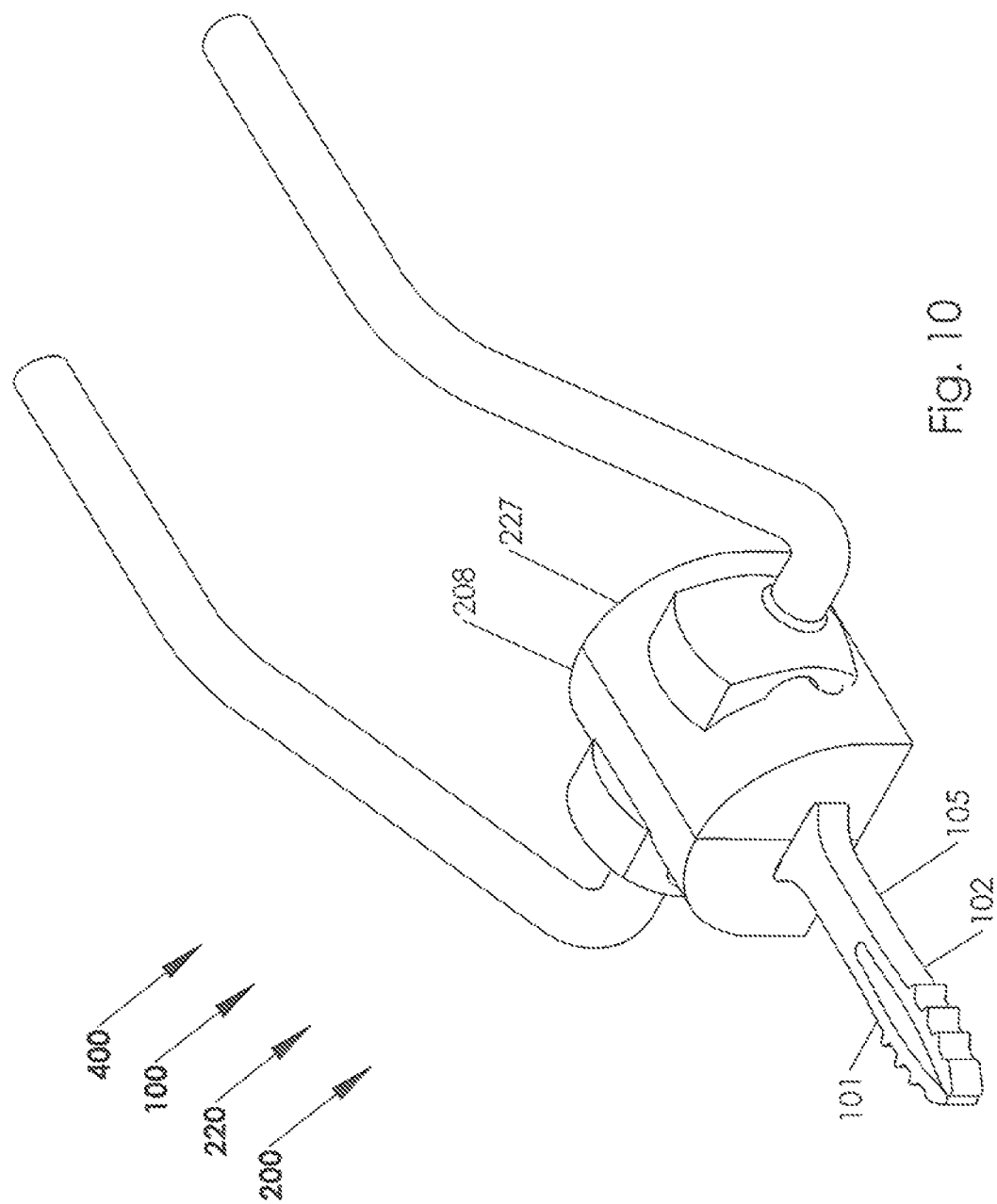

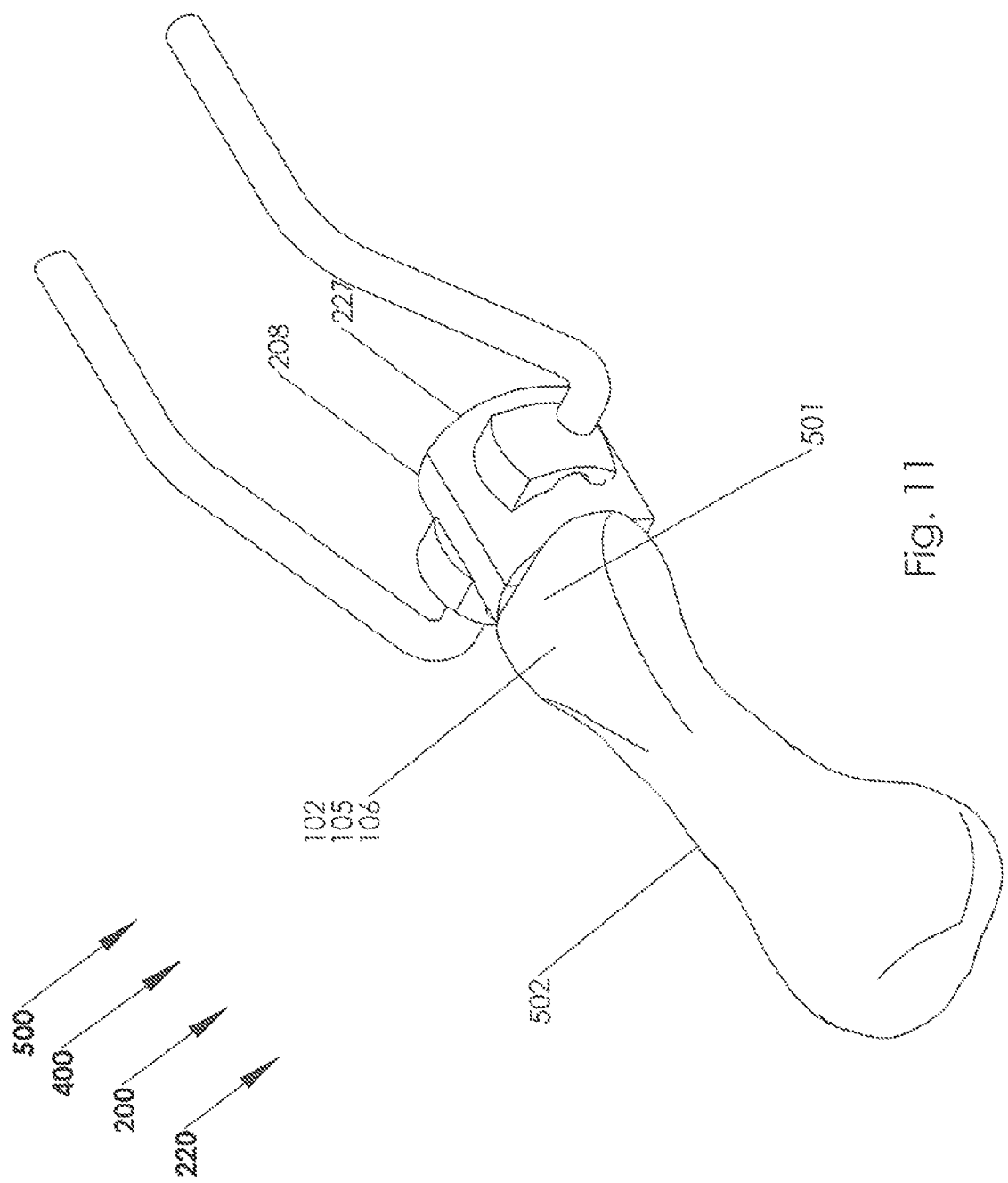

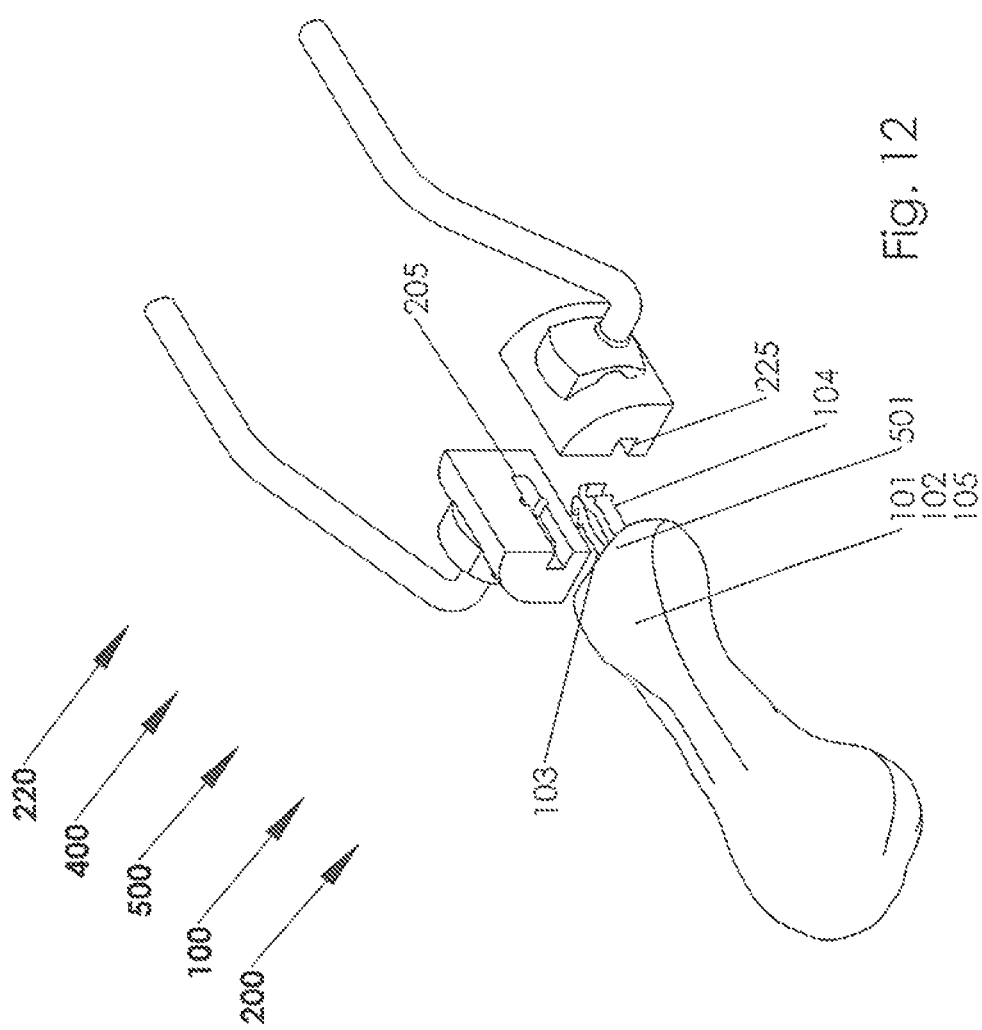

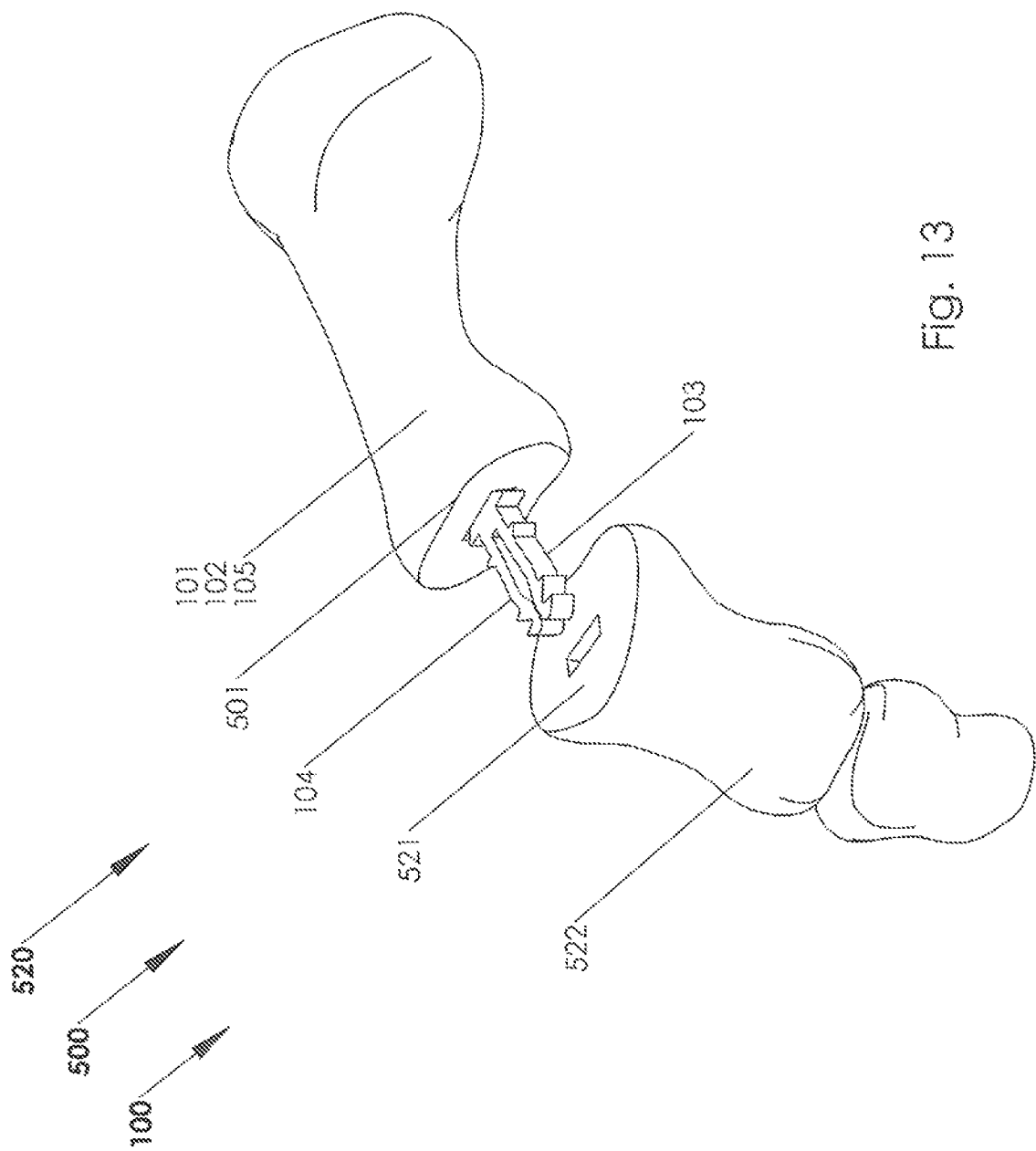

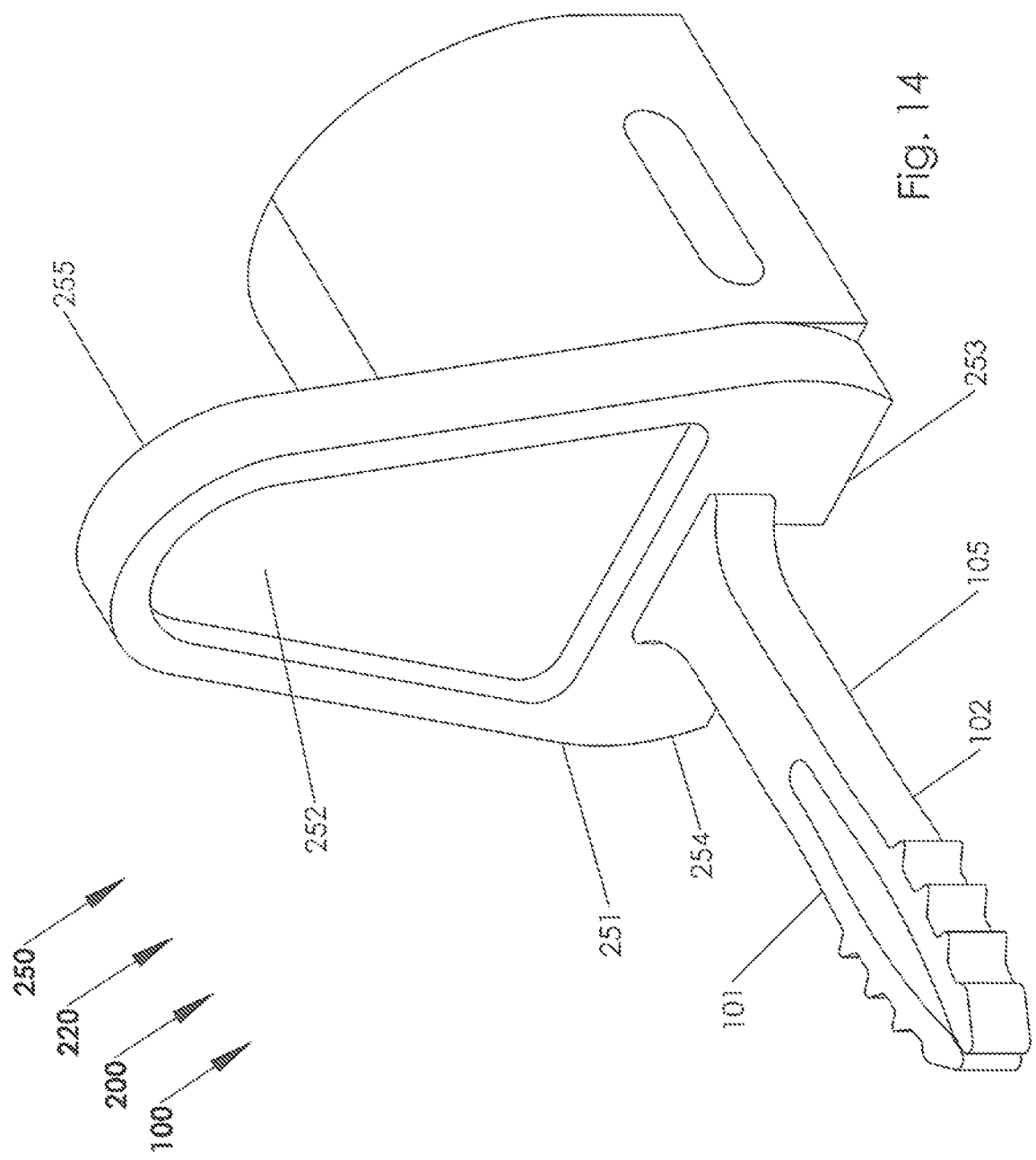

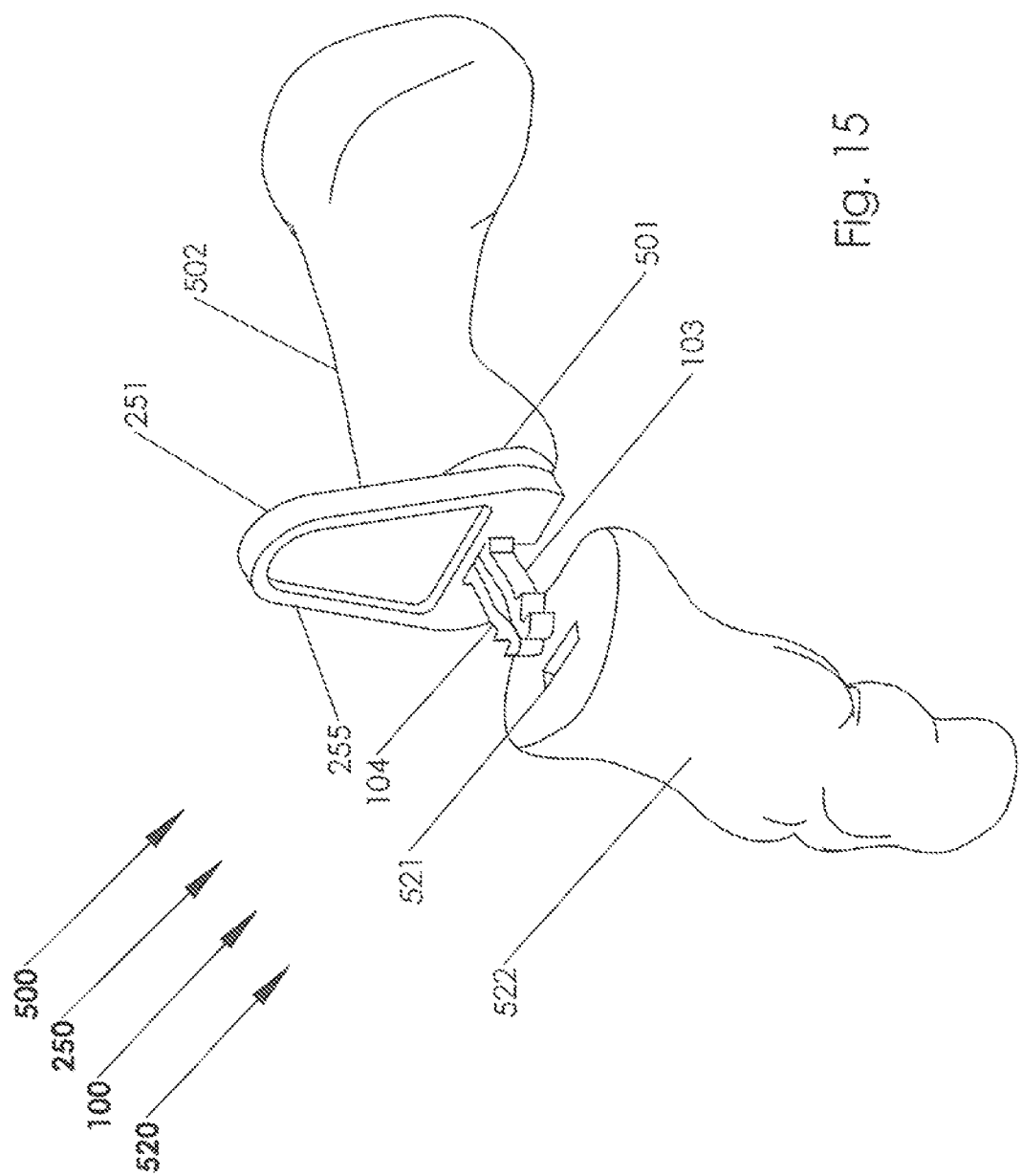

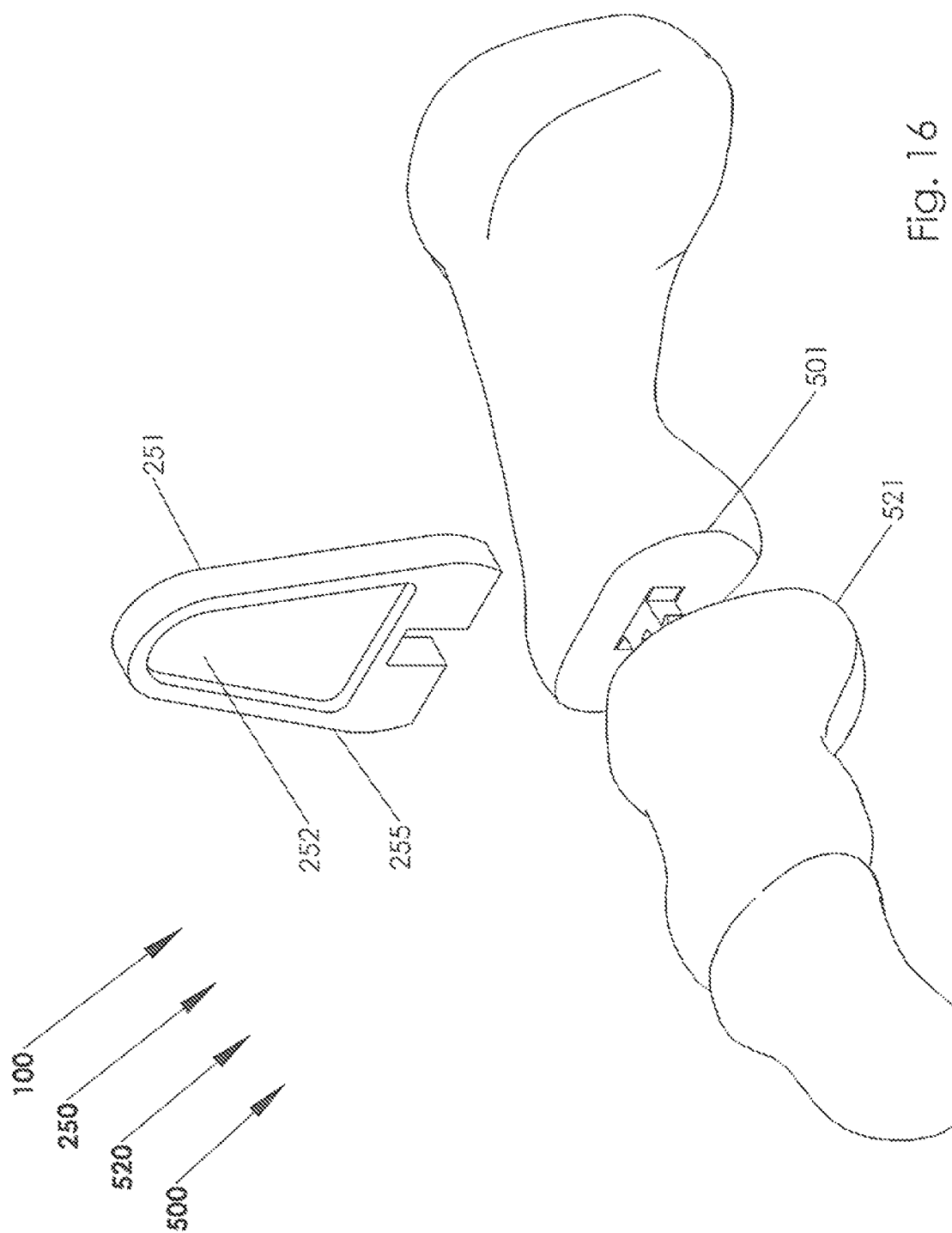

METHOD AND SYSTEM FOR STORING AND INSERTING AN IMPLANT

CROSS-REFERNCE TO RELATED APPLICATION

This application is a divisional of patent application Ser. No. 12/924,733, which was filed Oct. 4, 2010.

BACKGROUND OF THE INVENTION

1. Field of the Invention

The present invention relates to a method and system for constraining, protecting, insulating, and inserting orthopedic implants.

2. Description of the Related Art

Fusion of bones in orthopedics often involves metallic implants being attached to bones to fixate them together during the healing process. In certain small hone procedures, such as the fusion of toe or finger bones, it is difficult to use metallic implants that attach to the cortex of the bone because there is limited bone surface area. In these procedures, it is often desirable to use intramedullary implants that insert into the medullary canal of two adjacent bones and thus fixate them to each other. Implants made from shape memory materials, such as nitinol, are particularly suited for this approach because they can be inserted into the two bones, expand upon warming by the body, and thus fixate bones to one another.

However, the process of constraining, protecting, insulating, inserting, and positioning such an implant during the surgical procedure is difficult. Some existing shape memory implants are simply held by a pair of forceps, exposed to air, and are thus susceptible to premature shape change from operating room temperatures. Premature shape change renders the implant useless.

It also can be difficult to insert and impact a small intramedullary implant into hard bone without damaging the implant. Striking the implant with a mallet can deform the implant or damage its biocompatible surface finish. Similarly, intramedullary implants for use in larger bones are also difficult to constrain, insulate, and/or insert.

Orthopedic implants also may be shaped to conform to anatomy. For example, an intramedullary implant for use in toe fusions might feature an angle such that when the toe heals it is angled downward in a normal anatomic position. An implant of this type, with a bend or curve, is more difficult to hold and insert because subjecting the implant to a linear impacting force that passes through a bend might cause the implant to be deformed or damaged.

An intramedullary implant is also difficult to position properly. If it is placed into one bone first, for example, it can then be dislodged and moved out of position by the process of inserting into a second bone.

Other companies have commercialized plastic storage blocks for shape memory implants. These blocks serve the sole purpose of constraining the implant in a deformed state. For example, BioMedical Enterprises, Inc., Memometal, Inc., Biopro, Inc., and Core Essence Orthopedics all sell shape memory implants that are stored in plastic blocks. The blocks constrain the implant, but do not insulate the shape-changing portion of the implants, cannot be impacted, do not protect the implant during the insertion process, and do not assist in positioning the implant in the proper anatomic orientation. In U.S. Pat. No. 4,665,906, Jervis refers to a method for restraining a shape memory device, however, no images of such a device are provided. In U.S. Publication 2009/0018556, Prandi describes a surgical instrument that manipulates a shape memory implant for insertion into bone. This device does not allow for impacting the implant into position, does not protect the implant from metal-on-metal surface marring, and does not insulate the implant in any way.

Accordingly, a method and apparatus for constraining, protecting, insulating, inserting, and positioning an orthopedic implant is desirable. The apparatus can be made to accommodate any shape of implant to permit simple insertion.

SUMMARY OF THE INVENTION

In accordance with the present invention, a method and apparatus for constraining, protecting, insulating, inserting, and positioning an orthopedic implant holds an implant during certain orthopedic procedures so that it can be easily and properly placed into the body. The method and apparatus includes a restraining block having an impact surface. The restraining block engages an implant at a first end, and further a medical instrument engages the restraining block and positions the restraining block at a bone such that the impact surface may be impacted to insert a second end of the implant into the bone. The holding of a first end of the implant within the restraining prevents the implant from being over inserted into the bone.

The restraining block includes an implant engagement feature that receives the first end of the implant therein thereby constraining the implant in a deformed shape. The restraining block further includes and an instrument engagement feature engageable by the medical instrument. Once the instrument engagement feature has been engaged by a medical instrument, the instrument engagement feature deforms such that the restraining block remains attached to the medical instrument.

The method and apparatus further includes a base block that engages the implant at the second end. The base block includes an implant engagement feature that receives the second end of the implant therein thereby constraining the implant in a deformed shape. The base block further includes a restraining block engagement feature that receives the restraining block therein.

It is therefore an object of the present invention to constrain an implant in a shape designed for insertion, insulate the implant from operating room temperatures for as long as possible, provide a graspable surface for manipulating and inserting the implant without damaging it, and positioning the implant anatomically for ideal performance.

It is a further object of the present invention to define a method for constraining, insulating, inserting, and positioning an orthopedic implant.

It is still a further an object of the present invention to provide an apparatus that allows for the grasping and impacting of an implant that is not straight, and which would normally be difficult to insert.

Still other objects, features, and advantages of the present invention will become evident to those of ordinary skill in the art in light of the following. Also, it should be understood that the scope of this invention is intended to be broad, and any combination of any subset of features elements, or steps described herein is part of the intended scope of the invention.

BRIEF DESCRIPTION OF THE DRAWINGS

FIG. 1a provides an isometric view of an orthopedic implant in an original (first) shape.

FIG. 1b provides an isometric view of an orthopedic implant in a deformed (second) shape.

FIG. 2a provides an inside isometric view of a restraining block first clamshell.

FIG. 2b provides an outside isometric view of a restraining block first clamshell.

FIG. 2c provides an inside isometric vie of a restraining block second clamshell.

FIG. 2d provides an outside isometric vies of a restraining block second clamshell.

FIG. 4 provides an isometric view of a base block.

FIG. 5 provides an isometric view of restraining block clamshells and an orthopedic implant inserted into a base block.

FIG. 6 provides an isometric view of a medical instrument.

FIG. 7 provides a close-up isometric view of the tips of the medical instrument.

FIG. 8 provides an isometric view of a medical instrument engaging a restraining block.

FIG. 9 provides an isometric view of a medical instrument engaging a restraining block, with the restraining block holding an orthopedic implant in a second shape in a base block.

FIG. 10 provides an isometric view of a medical instrument engaging a restraining block, with the orthopedic implant legs exposed and ready for insertion into bone.

FIG. 11 provides an isometric view of a medical instrument engaging a restraining block with the implant inserted into a first bone and changing to the first shape.

FIG. 12 provides an isometric view of a medical instrument opening and removing the restraining block.

FIG. 13 provides an isometric view of a second bone being pulled over the implant.

FIG. 14 provides an isometric view of a restraining block and an arresting tab according to an alternative embodiment engaging an orthopedic implant and constraining it in a second shape.

FIG. 15 provides an isometric view of an arresting tab according to an alternative embodiment constraining an orthopedic implant in a second shape.

FIG. 16 provides an isometric view of an arresting tab according to an alternative embodiment being removed and releasing an orthopedic implant to engage a second bone.

DETAILED DESCRIPTION OF THE PREFERRED EMBODIMENTS

Figure 3:
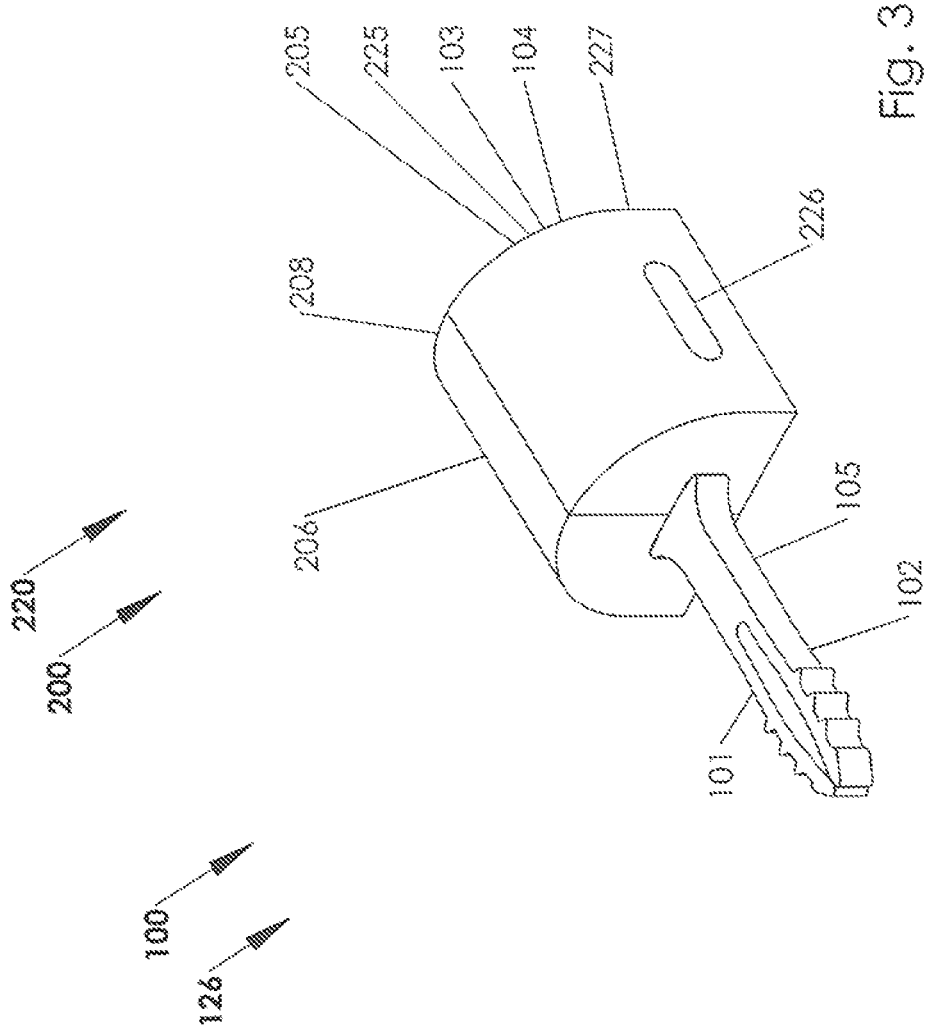
FIG. 3 provides an isometric view of a restraining block engaging and constraining an orthopedic implant in a second shape.

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Shape-memory devices can be used by orthopedic surgeons to compress and fixate one bone to another to assist in healing. Examples of shape-memory effect materials include, but are not limited to nitinol, AuCd, $FePt_3$, beta Brass, and InTI. Shape-memory materials allow a medical implant to be formed in an original state, deformed while in a cold martensitic state, and then heated to a point where the deformed implant changes from the martensitic state to an austenitic state, thereby returning the deformed implant to its original state. Upon cooling, the medical implant remains in the original state. Accordingly, the implant has an original, or first shape, and a deformed, or second shape. It is important to keep the implants constrained and insulated in the second shape prior to surgical use. If they are not constrained and insulated, then the implants might prematurely transition from the second shape to the first shape, and be rendered unusable to the surgeon.

In this invention, a method and system for constraining, insulating, and inserting a shape memory medical implant are described. As shown in FIGS. 1A and 1B, a medical implant 100, fabricated from shape memory material, has a first shape 125, and a second shape 126. The implant 100 has a first end with a first leg 101 and a second leg 102 for insertion into a bone. The implant 100 also has a second end with a first arm 103 and a second arm 104 for insertion into a second bone. The implant 100 has a body 105 that connects the legs 101 and 102 to the arms 103 and 104.

A restraining block is shown in FIGS. 2A-2D. The restraining block can be manufactured from a single component, or consist of multiple components. In FIGS. 2A-2D, the restraining block consists of two halves, referred to as clamshells below for clarity. FIGS. 2A and 2B show a first clamshell 200 in an inside view 201 and an outside view 202. The first clamshell 200 has an implant engagement feature 205 and an instrument engagement feature 206. Both engagement features 205 and 206 are depicted as slots in the preferred embodiment, but might be any number of other shapes such as holes, tabs, or any type of mating surface that serves as an engagement feature. The first clamshell 200 also has an impacting surface 208. FIGS. 2C and 2D show a second clamshell 220 in an inside view 221 and an outside view 222. The second clamshell 220 has an implant engagement feature 225 and an instrument engagement feature 226. The second clamshell 220 also has an impacting surface 227. The two components of this restraining block embodiment, consisting of clamshells 200 and 220, may be fabricated from any firm but deformable and insulating material suitable for medical use, such as certain plastics. While the restraining block has been referred to as a clamshell and includes a first clamshell 200 and a second clamshell 220, those of ordinary skill in the art will recognize that the restraining block may be a single piece or any number of pieces designed to include an implant engagement feature and an instrument engagement feature.

FIG. 3 shows the implant 100 in the second shape 126 being held in a restraining block consisting of a first clamshell 200 and a second clamshell 220. The implant engagement feature 205 engages the arm 103, and the implant engagement feature 225 engages the arm 104. The arms 103 and 104 are constrained from motion and insulated by the restraining block clamshells 200 and 220. The implant legs 101 and 102 and the implant body 105 are not constrained by the restraining block clamshells 200 and 220.

FIG. 4 shows a base block 300. The base block 300 may be fabricated from any hard and insulating material suitable for medical use, such as certain plastics. The base block 300 has a second slot 301 and a first slot 302. The base block 300 also has a restraining block engagement feature 303 depicted as a cavity in the preferred embodiment, and an implant engagement feature 304 that permits interfacing with implant 100.

FIG. 5 shows how the medical implant 100 and the restraining block are inserted into the base block 300 after the medical implant 100 has been inserted into the restraining block. The instrument engagement feature 226 of the restraining block second clamshell 220 aligns with the slot 301 of the base block 300. Similarly, the instrument engagement feature 206 of the restraining block first clamshell 200 aligns with the slot 302 of the base block 300. The legs 101 and 102 and the implant body 105 fit into and are constrained and insulated by the slot 304 of the base block 300.

FIG. 6 shows a medical instrument 400. The medical instrument 400 can be fabricated from any material suitable for medical instruments, such as metal or plastic. The medical instrument 400 can be any number of shapes and designs as desired by a surgeon, but is depicted as a forceps in the preferred embodiment. The medical instrument 400 has a second tip 401 and a first tip 402 for grasping. In this embodiment, a ratchet 403 allows the forceps 400 to lock into position when desired by the surgeon.

FIG. 7 shows a close up view of the instrument 400 and the tips 401 and 402. There is a first engagement projection 403 on the instrument tip 401, and a second engagement projection 404 on the instrument tip 402.

FIG. 8 shows the instrument 400 grasping the restraining block second clamshell 220 and the first clamshell 200. The engagement projection 403 on the instrument 400 inserts into the instrument engagement feature 226 on the second clamshell 220. Similarly, the engagement projection 404 on the instrument 400 inserts into the instrument engagement feature 206 on the first clamshell 200. The medical instrument 400 is made from a material that is harder than the restraining block clamshells 200 and 220. The engagement projections 403 and 404 on the instrument 400 are slightly bigger than the instrument engagement features 206 and 226 on the restraining block clamshells 200 and 220, thus deforming the two features 206 and 226 when the instrument 400 is closed and creating a press fit connection.

FIGS. 9 through 13 show a sequential depiction of how the invention operates.

FIG. 9 shows a complete assembly of the implant and storage system, The implant 100 is constrained by the restraining block first and second clamshells 200 and 220. The implant 100 and restraining block clamshells 200 and 220 are in turn held within the base block 300. The medical instrument 400 is used to grasp the restraining block clamshells 200 and 220.

FIG. 10 shows the medical instrument 400 grasping the restraining block clamshells 200 and 220, which in turn constrain the implant 100. The legs 101 and 102 and the body 105 of the implant 100 are now removed from the base block 300 and are no longer insulated by the base block 300. The implant 100 remains in the second shape 126 until the legs 101 and 102 are warmed. The impacting surfaces 208 and 227 have been brought together by instrument 400 and can be tapped or impacted by a surgeon to insert the implant 100.

FIG. 11 shows a typical finger or toe bone 500 with implant 100 being inserted. The bone 500 has a body 502 and an end 501. Instrument 400 grasps the restraining block clamshells 200 and 220 and allows implant 100 to be inserted into end 501 of bone 500. The impacting surfaces 208 and 227 allow a surgeon to tap or impact the implant 100 into bone 500. The legs 101 and 102 and the body 105 of implant 100 are impacted into end 501 of bone 500. The restraining block clamshells 200 and 220 still insulate, constrain, and protect the arms 103 and 104 of implant 100. Moreover, the restraining block clamshells 200 and 220 prevent over-insertion of the implant 100 into the bone 500 because the abutment of the restraining block clamshells 200 and 220 against the bone 500 arrests the insertion of the implant 100. The legs 101 and 102 are warmed by the body temperature of bone 500, and transform from the second shape 126 to the first shape 125.

FIG. 12 shows the legs 101 and 102 and the body 105 of the implant 100 now embedded in the end 501 of bone 500. Medical instrument 400 has been opened, allowing the restraining block 200 and 220 and the implant engagement features 205 and 225 to separate from and expose the implant arms 103 and 104. Because the engagement projections 403 and 404 on instrument 400 have press fit into the engagement features 206 and 226 of the clamshells 200 and 220, the clamshells 200 and 220 adhere to the instrument tips 401 and 402 when instrument 400 is opened.

FIG. 13 shows the implant 100 inserted into the end 501 of bone 500. A second bone 520 with an end 521 and a body 522 is shown being pulled over the arms 103 and 104 of the implant 100. Because the implant arms 103 and 104 were insulated by the restraining block clamshells 200 and 220, they remain in the second shape 126 until inserted into the bone 520. After insertion into the bone 520, the arms 103 and 104 transform from the second shape 226 to the first shape 125.

In an alternative embodiment, FIG. 14 shows the same restraining block clamshells 200 and 220 grasping the implant 100 while an arresting tab 250 is introduced. The arresting tab 250 is introduced by allowing bottom edges 253 and 254 of the arresting tab 250 to slip over the arms 103 and 104 of implant 100. A front surface 251 of the arresting tab 250 exists to position the implant 100 while the back surface 255 of the arresting tab 250 is in contact with the restraining block clamshells 200 and 220. The legs 103 and 104 and the body 105 of the implant 100 are not affected by the arresting tab 250. A recess 252 on both sides of the arresting tab 250 allows for a surgeon's fingers to grasp the arresting tab 250. The arresting tab 250 can have any number of shapes that allows the tab to be grasped a surgeon's fingers or a medical instrument.

In the alternative embodiment, FIG. 15 shows how the arresting tab 250 functions. As shown in FIG. 15, legs 101 and 102 and body 105 of implant 100 have already been inserted into end 501 of bone 500. The restraining block clamshells 200 and 220 have already been released by instrument 400, and the arms 103 and 104 of the implant 100 are now exposed. The arresting tab 250 is still engaged to the legs 101 and 102 of implant 100 such that the front surface 251 of the arresting tab 250 is now pressed against the end 501 of bone 500. Surface 251 of the arresting tab 250 effective positions and holds implant 100 in the desired anatomic location with respect to bone 500. A second bone 520 with end 521 is then pulled over the arms 103 and 104 of the implant 100, and surface 251 holds and prevents implant 100 from being dislodged.

In the final stage of the alternative embodiment, FIG. 16 shows the arresting tab 250 being lifted away from implant 100 by a surgeon grasping recess 252 on arresting tab 250. The arresting tab 250 accordingly holds implant 100 in a proper orientation within the bones 500 and 520 while the implant 100 is being inserted into the bones 500 and 501.

Although the present invention has been described in terms of the foregoing preferred and second embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

What is claimed:

1. A method of constraining an implant in an implant storage system, comprising:
   a. providing the implant including a first end and a second end, wherein the first end of the implant includes an implanted shape and an insertion shape;
   b. inserting the first end of the implant into a restraining block by placing a first component of the restraining block adjacent a second component of the restraining block with the first end of the implant therebetween;
   c. manipulating the restraining block to place the first end of the implant into its insertion shape by engaging the first and second components of the restraining block with a medical instrument and using the medical instrument to move the first and second components into an abutting relationship that constrains the first end of the implant in its insertion shape; and
   d. inserting the restraining block into a base block such that the restraining block maintains the first end of the implant in its insertion shape.

2. The method of constraining an implant in an implant storage system according to claim 1, further comprising inserting the second end of the implant into the base block.

3. The method of constraining an implant in an implant storage system according to claim 2, wherein inserting the second end of the implant into the base block constrains the second end of the implant in an insertion shape.

4. A method of inserting an implant into bone, comprising:
   a. engaging with a medical instrument a restraining block having therein a first end of the implant;
   b. removing with the medical instrument the restraining block from a base block;
   c. inserting with the medical instrument a second end of the implant into a first bone;
   d. opening the medical instrument thereby releasing the first end of the implant from the restraining block;
   e. pulling a second bone over the first end of the implant.

5. The method of inserting an implant into bone according to claim 4, wherein step c comprises tapping the restraining block with a blunt object to insert the second end of the implant into the first bone.

6. The method of inserting an implant into bone according to claim 4, wherein removing the restraining block from the base block releases the second end of the implant from the base block.

7. The method of inserting an implant into bone according to claim 6, wherein the base block constrains the second end of the implant in an insertion shape prior to the release of the second end of the implant from the base block.

8. A method of inserting an implant into bone, comprising:
   a. providing the implant including a first end and a second end, wherein the first end of the implant includes an implanted shape and an insertion shape;
   b. engaging the first end of the implant with a restraining block such that the restraining block constrains the first end of the implant in its insertion shape;
   c. engaging the restraining block with a medical instrument to maintain the first end of the implant constrained in its insertion shape;
   d. positioning the restraining block adjacent a first bone using the medical instrument, thereby locating the second end of the implant at the first bone;
   e. inserting with the medical instrument the second end of the implant into the first bone;
   f. opening the medical instrument thereby releasing the first end of the implant from the restraining block;
   g. pulling a second bone over the first end of the implant.

9. The method of inserting an implant into bone according to claim 8, wherein step e comprises tapping the restraining block with a blunt object to insert the second end of the implant into the first bone.

10. The method of inserting an implant into bone according to claim 8, wherein engaging the first end of the implant with the restraining block comprises placing a first component of the restraining block adjacent a second component of the restraining block with the first end of the implant therebetween.

11. The method of inserting an implant into bone according to claim 10, wherein engaging the restraining block with the medical instrument comprises engaging the first and second components of the restraining block with the medical instrument and using the medical instrument to move the first and second components into an abutting relationship that constrains the first end of the implant in its insertion shape.

* * * * *